(12) United States Patent
Sheinin et al.

(10) Patent No.: US 10,902,937 B2
(45) Date of Patent: Jan. 26, 2021

(54) LOSSLESS COMPRESSION OF DNA SEQUENCES

(71) Applicant: INTERNATIONAL BUSINESS MACHINES CORPORATION, Armonk, NY (US)

(72) Inventors: Vadim Sheinin, Yorktown Heights, NY (US); Hangu Yeo, Baldwin Place, NY (US)

(73) Assignee: International Business Machines Corporation, Armonk, NY (US)

( * ) Notice: Subject to any disclaimer, the term of this patent is extended or adjusted under 35 U.S.C. 154(b) by 473 days.

(21) Appl. No.: 14/178,619

(22) Filed: Feb. 12, 2014

(65) Prior Publication Data

US 2015/0227686 A1    Aug. 13, 2015

(51) Int. Cl.
*G16B 30/00* (2019.01)
*G16B 50/00* (2019.01)

(52) U.S. Cl.
CPC .............. *G16B 30/00* (2019.02); *G16B 50/00* (2019.02)

(58) Field of Classification Search
None
See application file for complete search history.

(56) References Cited

U.S. PATENT DOCUMENTS

| 8,554,492 | B2 | 10/2013 | Ahn et al. |
| 2004/0153255 | A1 | 8/2004 | Ahn |
| 2013/0166518 | A1 | 6/2013 | Mande et al. |

FOREIGN PATENT DOCUMENTS

| WO | 2004/070029 | 8/2004 |
| WO | 2012/092821 | 7/2012 |

OTHER PUBLICATIONS

Afify et al., "DNA Lossless Differential Compression Algorithm Based on Similarity of Genomic Sequence Database", International Journal of Computer Science & Information Technology (IJCSIT), vol. 3, No. 4, Aug. 2011, pp. 145-154.
Bonfield et al., "Compression of FASTQ and SAM format Sequencing Data", PLoS One 8(3): e59190. doi:10.1371/journal.pone. 0059190, Mar. 2013. (11 pages).
Chern et al., "Reference Based Genome Compression", IEEE Information Theory Workshop (ITW) 2012, Apr. 2012. (5 pages).
Fritz et al., "Efficient Storage of High Throughput DNA Sequencing Data Using Reference-Based Compression", Genome Research, 21(5):734-740, May 2011.

(Continued)

*Primary Examiner* — Joseph Woitach
(74) *Attorney, Agent, or Firm* — Tutunjian & Bitetto, P.C.; Vazken Alexanian (57) ABSTRACT

There is provided an apparatus and a processor-implemented method. The method includes aligning a reference genome with a plurality of DNA sequences. Each of the plurality of DNA sequences has a respective plurality of bases. The method further includes classifying and sorting the plurality of read sequences based on respective numbers of mismatched bases within the plurality of read sequences to obtain a plurality of re-arranged DNA sequences. The method also includes building a histogram based on respective positions of mismatched bases within the plurality of re-arranged DNA sequences. The method additionally includes coding at least some of the plurality of re-arranged DNA sequences based on the histogram.

20 Claims, 7 Drawing Sheets
Specification includes a Sequence Listing.

(56) References Cited

OTHER PUBLICATIONS

Jones et al., "Compression of next-generation sequencing reads aided by highly efficient de novo assembly", Nucleic Acids Research, Aug. 2012, pp. 1-9.
Kozanitis et al., "Compression Genomic Sequence Fragments Using SlimGene", Journal of Computational Biology, vol. 18, No. 3, Mar. 2011, pp. 401-413.
Mahoney, "The FASTQZ Compression Algorithm for FASTQ Files", Dell, Inc., Google Docs, Mar. 2012. (21 pages).
Popitsch et al., "NGC: Lossless and Lossy Compression of Aligned High-Throughput Sequencing Data", Nucleic Acids Research, Oct. 2012. (12 pages).

SEQUENCE LISTING

```
<160> NUMBER OF SEQ ID NOS: 4

<210> SEQ ID NO 1
<211> LENGTH: 49
<212> TYPE: DNA
<213> ORGANISM: Artificial Sequence
<220> FEATURE:
<223> OTHER INFORMATION: Randomly generated sequence for exemplary
      purposes

<400> SEQUENCE: 1
acacaatagc taagacccaa actgggatta gatacccac tatgcttag                    49

<210> SEQ ID NO 2
<211> LENGTH: 15
<212> TYPE: DNA
<213> ORGANISM: Artificial Sequence
```

```
<220> FEATURE:
<223> OTHER INFORMATION: Randomly generated sequence for exemplary
      purposes

<400> SEQUENCE: 2
tgggattaca taccc                                                        15

<210> SEQ ID NO 3
<211> LENGTH: 15
<212> TYPE: DNA
<213> ORGANISM: Artificial Sequence
<220> FEATURE:
<223> OTHER INFORMATION: Randomly generated sequence for exemplary
      purposes

<400> SEQUENCE: 3
agctaagacc caaac                                                        15

<210> SEQ ID NO 4
<211> LENGTH: 15
<212> TYPE: DNA
<213> ORGANISM: Artificial Sequence
<220> FEATURE:
<223> OTHER INFORMATION: Randomly generated sequence for exemplary
      purposes

<400> SEQUENCE: 4
acccagactg gaatt                                                        15
```

LOSSLESS COMPRESSION OF DNA SEQUENCES

BACKGROUND

Technical Field

The present invention relates generally to deoxyribonucleic acid (DNA) sequences and, in particular, to improving lossless compression of DNA sequences.

Description of the Related Art

Advances in genomics during the past ten years have increased the generation of deoxyribonucleic acid (DNA) sequence data and reduced the cost to generate the data. The cost to generate a genome has decreased from about $100,000,000 in 2001 to $10,000 in 2012, and can be less than $1,000 within a couple of years. As a result, the amount of genomics data is increasing exponentially. For example, accessed in May 2012, New York Genome Center (NYGC) had a plan to produce 9,000 TB of genomics data within the next several years. Hence, it created a need to store and transfer very large volumes of data efficiently.

Although general purpose compression algorithms such as GZIP, BZIP2 OR 7ZIP compress the DNA sequence reasonably well, their compression ratio is only around 3:1. The CRAM toolkit developed by the European Nucleotide Archive (ENA) is a reference-based compression toolkit and is widely used to compress DNA sequences. However, it is a set of Java tools and it is slow and the lossless compression ratio is not so impressive.

SUMMARY

According to an aspect of the present principles, a processor-implemented method is provided. The method includes aligning a reference genome with a plurality of DNA sequences. Each of the plurality of DNA sequences has a respective plurality of bases. The method further includes classifying and sorting the plurality of read sequences based on respective numbers of mismatched bases within the plurality of read sequences to obtain a plurality of re-arranged DNA sequences. The method also includes building a histogram based on respective positions of mismatched bases within the plurality of re-arranged DNA sequences. The method additionally includes coding at least some of the plurality of re-arranged DNA sequences based on the histogram.

According to another aspect of the present principles, an apparatus is provided. The apparatus includes a sequence aligner for aligning a reference genome with a plurality of DNA read sequences. Each of the plurality of DNA read sequences has a respective plurality of bases. The apparatus further includes a sequence classifier and sorter for classifying and sorting the plurality of read sequences based on respective numbers of mismatched bases within the plurality of read sequences to obtain a plurality of re-arranged DNA read sequences. The apparatus also includes a histogram builder for building a histogram based on indexes of mismatched bases within the plurality of re-arranged DNA read sequences. The apparatus additionally includes a processor-based coder for coding at least some of the plurality of re-arranged DNA read sequences based on the histogram.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles are directed to improving lossless compression of DNA sequences. In an embodiment, the present principles perform lossless compression of DNA sequences by exploiting the fact that most read sequences are matched perfectly to the reference genome and any two human genomes are more than 99% identical.

In an embodiment, the present principles are directed to the lossless compression of a DNA sequence stored in the reference based Sequence Alignment Map (SAM) file format. Lossless compression in accordance with the present principles has a better compression ratio than off-the-shelf general compression algorithms and the aforementioned CRAM toolkit. While one or more embodiments of the present principles involve and/or are otherwise describe the use of the reference based SAM file format, it is to be appreciated that the present principles are not limited to the preceding format, and thus, other formats can also be used in accordance with the present principles, while maintaining the spirit of the present principles. These and various other variations of the present principles are readily contemplated by one of ordinary skill in the art, while maintaining the spirit of the present principles.

Figure 1:
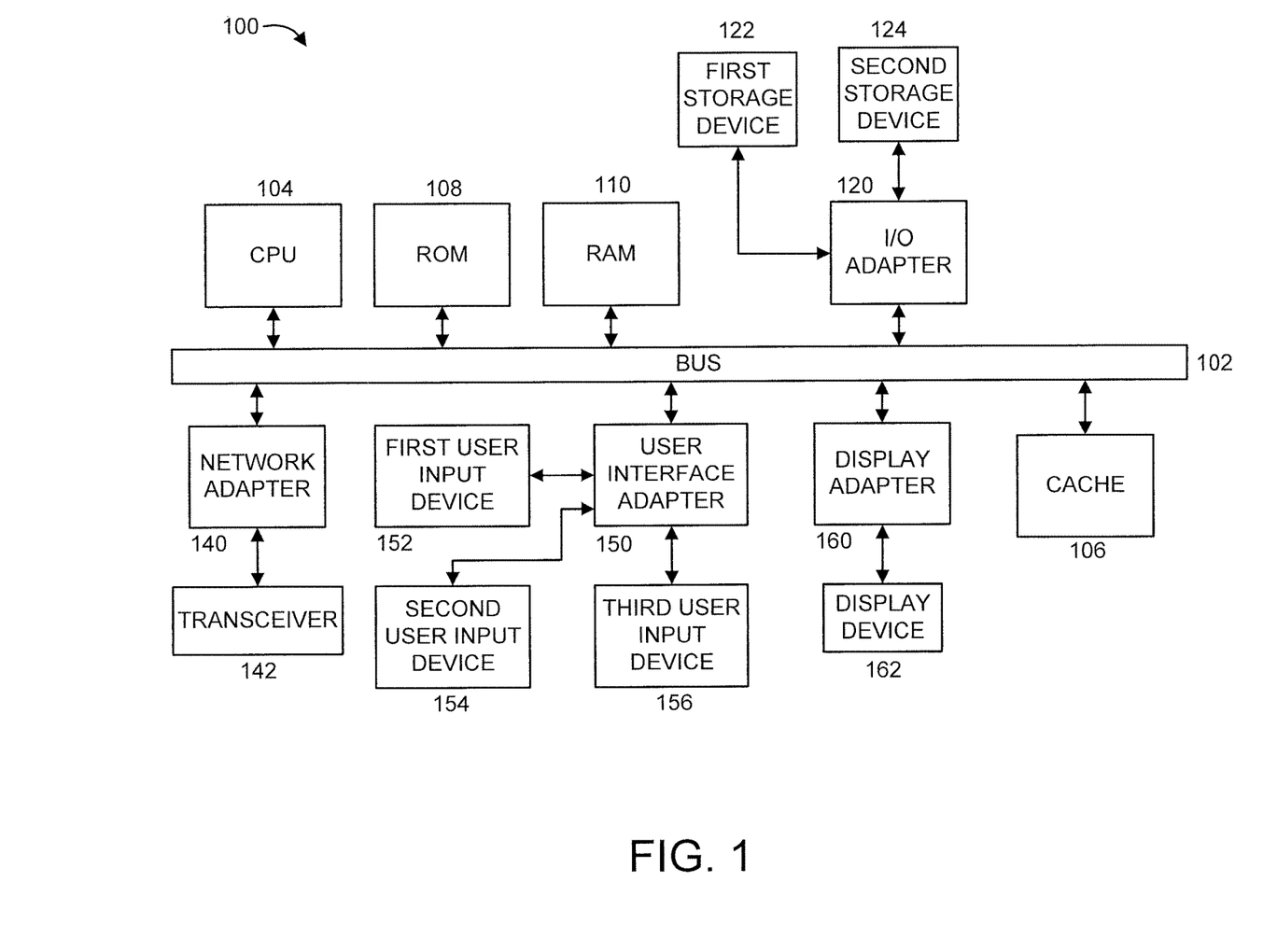
FIG. 1 shows an exemplary processing system 100 to which the present principles may be applied, in accordance with an embodiment of the present principles.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A transceiver 142 is operatively coupled to system bus 102 by network adapter 140.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

A display device 162 is operatively coupled to system bus 102 by display adapter 160.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
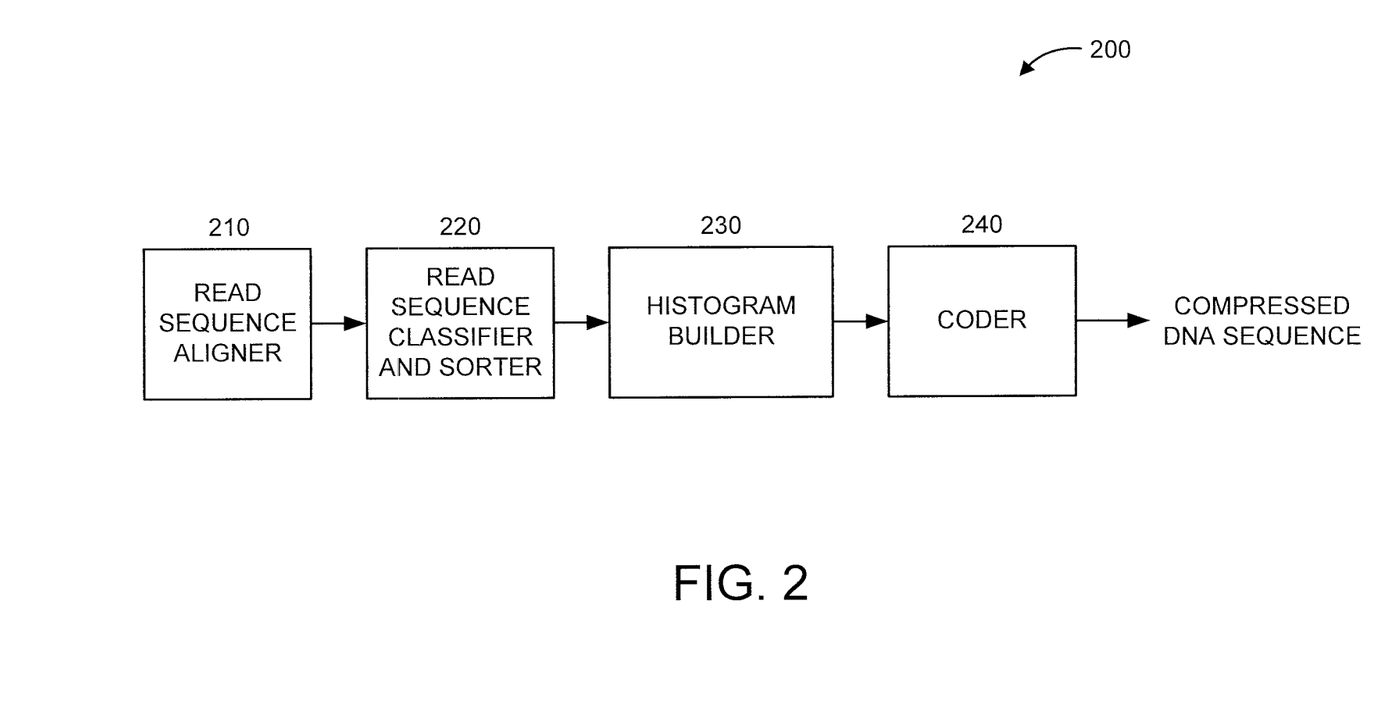
FIG. 2 shows an exemplary system 200 for lossless compression of DNA sequences, in accordance with an embodiment of the present principles.

Moreover, it is to be appreciated that system 200 described below with respect to FIG. 2 is a system for implementing respective embodiments of the present principles. Part or all of processing system 100 may be implemented in one or more of the elements of system 200.

Figure 4:
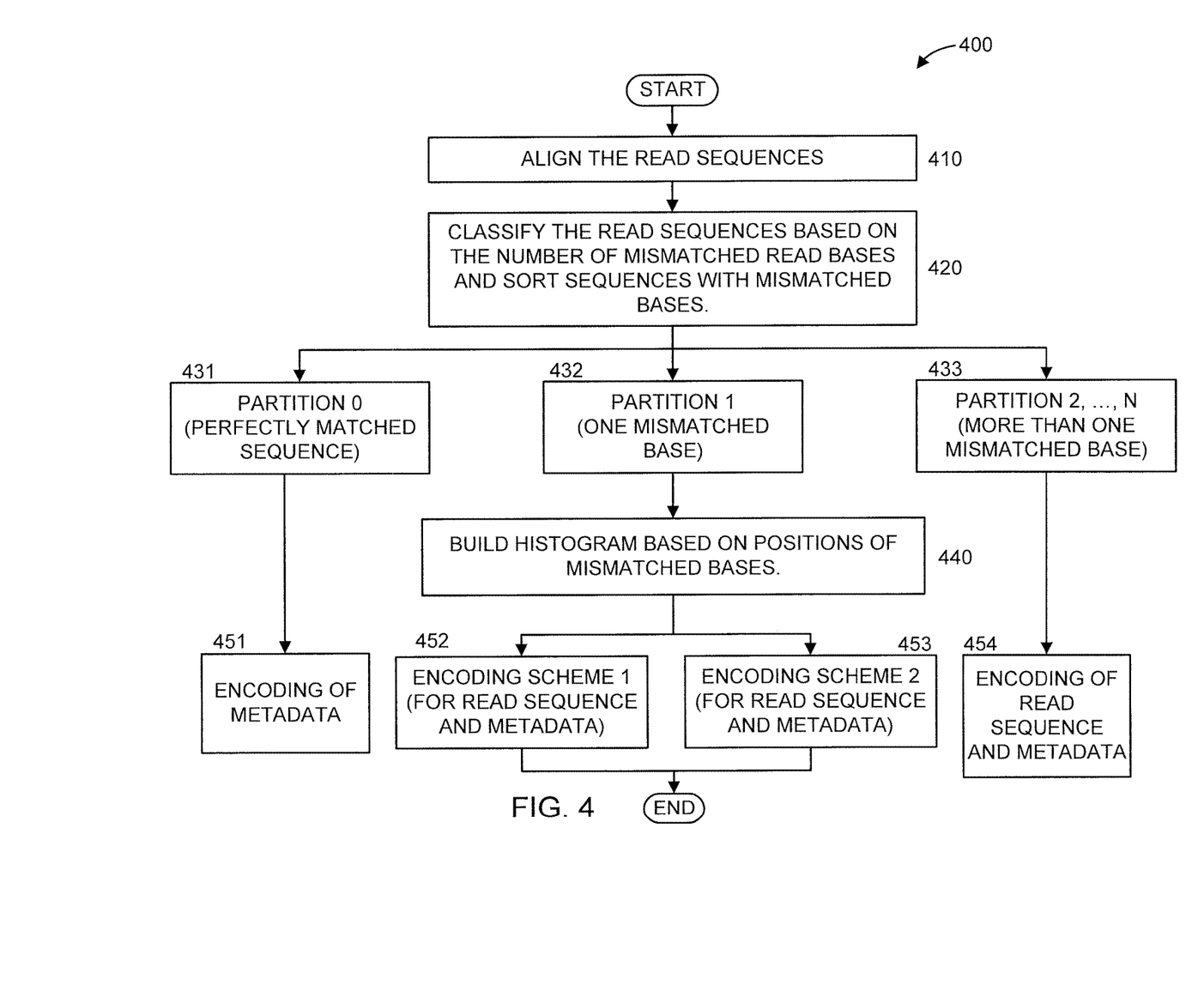
FIG. 4 shows an exemplary method 400 for read sequence compression, in accordance with an embodiment of the present principles.

Further, it is to be appreciated that processing system 100 may perform at least part of the method described herein including, for example, at least part of method 400 of FIG. 4. Similarly, part or all of system 200 may be used to perform at least part of method 400 of FIG. 4.

FIG. 2 shows an exemplary system 200 for lossless compression of DNA sequences, in accordance with an embodiment of the present principles. The system 200 includes a read sequence aligner 210, a read sequence classifier and sorter 220, a histogram builder 230, and a coder 240.

Coder can compress data using one or more of LZMA, GZIP, run-length coding, and so forth, depending upon the particular implementation. It is to be appreciated that the preceding compression techniques are merely illustrative and, thus, other compression techniques can also be used in accordance with the teachings of the present principles, while maintaining the spirit of the present principles.

Moreover, it is to be appreciated that while only a single coder 240 is shown in FIG. 2, in other embodiments, two or more coders can be used. For example, as shown and described with respect to FIG. 3, parsed header part 331 and parsed read sequence 332 are compressed in order to obtain a compressed header file 341 and a compressed sequence file 342 that, in turn, are further compressed to obtain a compressed header file 351 and a compressed read sequence file 352. All of the preceding compression can be performed by coder 240 using various compression techniques. However, in other embodiments, two or more coders can be used to perform the various compression techniques. To that end, we note that in an embodiment, the generation of compressed files 341 and 342 can involve two different coding techniques, namely differential coding and run-length coding, while the generation of compressed files 351 and 352 can involve GZIP, LZMA, and/or so forth. These and other variations of the elements of FIG. 2 are readily contemplated by one of ordinary skill in the art given the teachings of the present principles provided herein, while maintaining the spirit of the present principles.

In an embodiment, a reference based compression method is provided that efficiently compresses DNA sequences stored in the SAM file format. The SAM file include sequences of DNA bases, probabilities of a base calling mistake (quality value), and other supporting information. The inclusion of the quality values is optional. The SAM file aligned for FASTQ file includes quality values, but the SAM filed aligned for FASTA file format does not include quality information. We presume that the reference genome is available to both the encoding unit which compresses the sequence and the decoding unit which decompresses the compressed data without any additional external information. We further presume that read sequence order does not have any meaning for any given data set. The present principles can take advantage of a number of standard compression techniques such as, for example, but not limited to, run-length coding, differential coding and Lempel-Ziv-Markov chain Algorithm (LZMA) compression. That is, it is to be appreciated that while one or more particular compression techniques are described herein that are capable of being in accordance with the present principles, the present principles are not limited to solely the described compression techniques and, thus, other compression techniques can be used while maintaining the spirit of the present principles.

Figure 3:
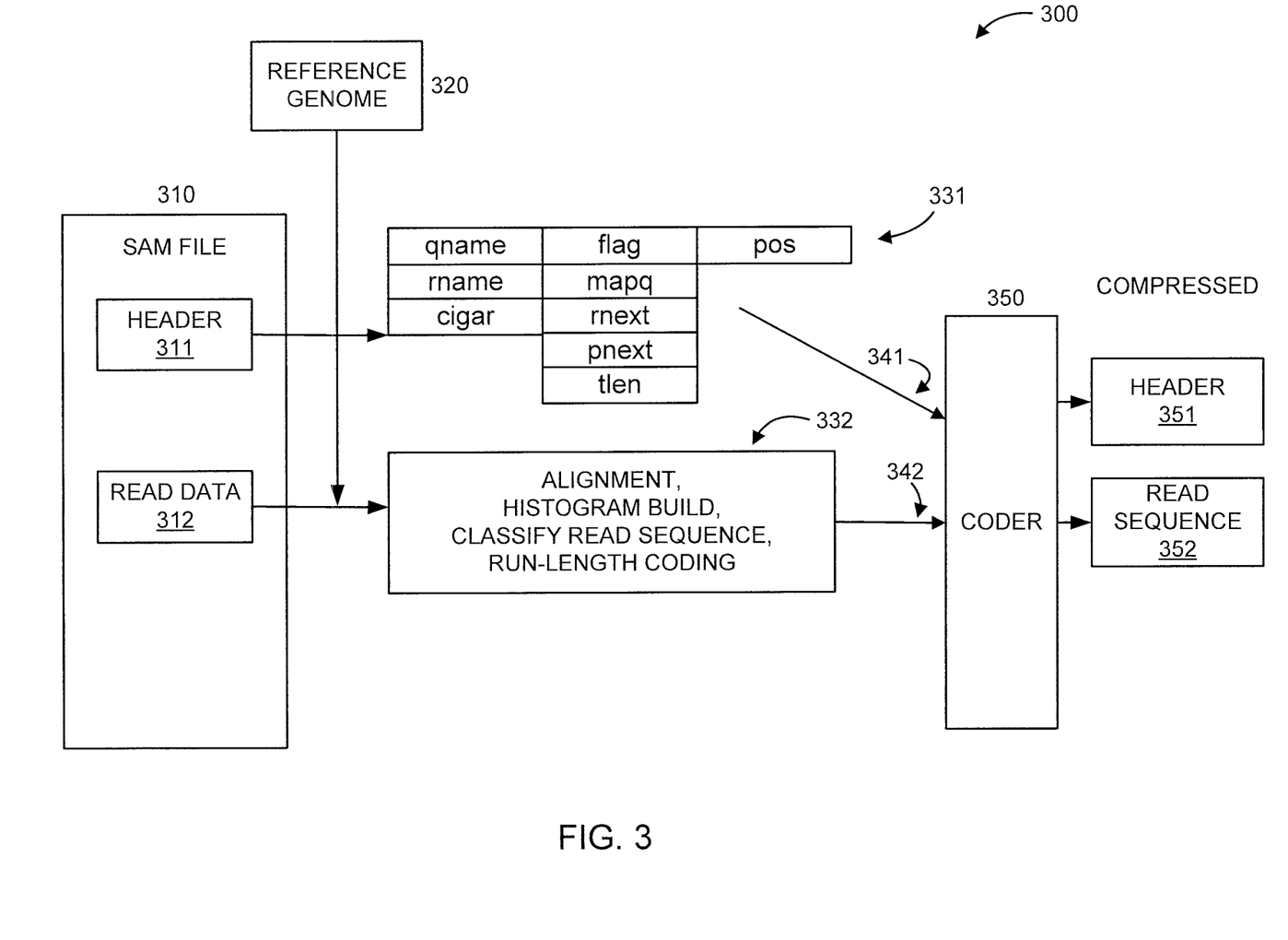
FIG. 3 shows an exemplary schematic overview 300 of a lossless compression method for DNA sequences, in accordance with an embodiment of the present principles.

FIG. 3 shows an exemplary schematic overview 300 of a lossless compression method for DNA sequences, in accordance with an embodiment of the present principles. The SAM file format stores aligned data associated with each sequence. The aligned data includes read sequences and nine fields of meta-data such as read names (rname), mapping position (pos), mapping patterns (cigar), and so forth. Thus, the SAM file format can be considered to include a header portion 311 and read data 312. The present principles take the aligned file 310 in the SAM file format as well as the reference genome 320 as input files, parse each line into a header part 331 and a read base sequence (read data) 332, and output two compressed files (one compressed file 341 for the header and another compressed file 342 for the read sequence). The parsed read bases are mapped to the reference genome 320 using matching header information such as read name (rname) and cigar string (cigar) as shown in part 331. The compressed header 341 and compressed mapped read bases 342 are further compressed separately by a coder 350 using, for example, LZMA and/or GZIP as depicted in the FIG. 3. In an embodiment, prior to being input to coder 350 for further compression, the read base sequence (read data) 332 as well as the qname, rname, cigar, and pos fields of header part 331 are differentially coded (with the pos field being pre-sorted prior to the differential coding), while the fields flag, mapq, rnext, pnext, and tlen of header part 331 are run-length coded.

The (initial) header compression is straight forward and simple. Each of nine mandatory fields is parsed and compressed separately using standard compression techniques such as, for example, but not limited to, run-length coding and differential coding techniques, to obtain compressed file 341. However, the mapping position field (pos) corresponding to perfectly match read sequences is presorted before it is encoded using a differential coder to enhance the performance. For a single-end read compression, the qname (query template name) fields are encoded into the compressed file, but we do not store the qname field information when we compress the paired-end DNA reads to improve the compression efficiency.

The read sequence is composed of four bases (A, T, G and C). A key feature of read sequence compression is run-length encoding based on classified and sorted read sequences. Run-length coding is a simple encoding scheme and works well when there are many strings of the same alphabets within the sequences. Generally, run-length coding is not effective to compress the read bases because the four bases randomly occur within the sequence without having any pattern. To improve the efficiency of the simple run-length coding technique, the read sequences are preprocessed in four steps as described below with respect to FIG. 4. The processed read sequences include long stretches of identical characters, and the run-length coding efficiency is improved dramatically.

Referring back to FIG. 3, the coding/compression portions of the method take a SAM file 310 and a reference genome 320 as input files, and generates a compressed header 341, a compressed read sequence 342 as output files. First, each line of data (sequence) in the SAM file 310 is parsed into header meta-data (9 fields) 331 and a read base sequence 332. Second, the parsed header 331 and read sequence 332 are independently encoded to generate the compressed header file 341, the compressed read sequence file 342, and the two encoded data files 341 and 342 are further compressed by coder 350 with general compression algorithms such as, for example, but not limited to, LZMA and GZIP, to output compressed header file 351, compressed read sequence file 352. In an embodiment, coder 350 corresponds to coder 240 shown in FIG. 2.

FIG. 4 shows an exemplary method 400 for read sequence compression, in accordance with an embodiment of the present principles. The method 400 can be described as a processor implemented method. In such a case, one of ordinary skill in the art would recognize that a memory would also be used to implement the method. The method 400 is used to obtain compressed read sequence file 342.

At step 410, align the read sequence to the reference genome using the cigar and rname fields in the header. Step 410 can be performed by, for example, read sequence aligner 210.

At step 420, classify the read sequences into partitions based on the number of mismatched bases within the sequence. The classification involves sorting the sequences with mismatched bases using the mismatched position as an index. Step 420 can be performed by, for example, classifier and sorter 220.

The outputs of the classification performed by step 240 are shown in blocks 431, 432, and 433. Block 431 corresponds to partition 0 which includes only perfectly matched sequences. Block 432 corresponds to partition 1 which includes only one mismatched base in the sequence. Block 433 corresponds to partitions 2 through N, which each include more than one mismatched base.

At step 440, build a histogram using the presorted read sequences classified into partition 1 (read sequences with a single mismatched base). Step 440 can be performed by, for example, histogram builder 230.

At step 451, encode the read sequences classified into partition 0 (perfectly matched sequences). The read sequences in this partition account for more than 70% of the total sequences, but this partition needs zero bits to encode because it is perfectly matched and the decoder does not need any information other than metadata to decode. The metadata fields corresponding to each sequence are sorted based on the position field. Step 451 can be performed by, for example, encoder 240.

At one of steps 452 and 453, encode the read sequences classified into partition 1. The read sequences of partition 1 are coded differently based on the distribution of histogram. At step 452, the histogram is not evenly distributed (with one or more peaks) and, thus, the read sequences are encoded using column-wise run-length scheme (encoding scheme 1, per step 452). At step 453, the histogram is evenly distributed without any peaks and, thus, two encoded strings are constructed. In one string, the bases are run-length coded, and the indexes of the mismatched bases are run-length coded in the second string. Steps 452 and 453 can be performed by, for example, encoder 240.

At step 454, read sequences classified into partitions 2, 3, . . . N (more than one mismatched bases) accounts for less than 15% of total input read sequences, and are sorted and run-length coded. Step 454 can be performed by, for example, encoder 240

Thus, only metadata is encoder for partition 0, and both metadata and read sequence data are encoded for partitions 1 through N.

Figure 5:
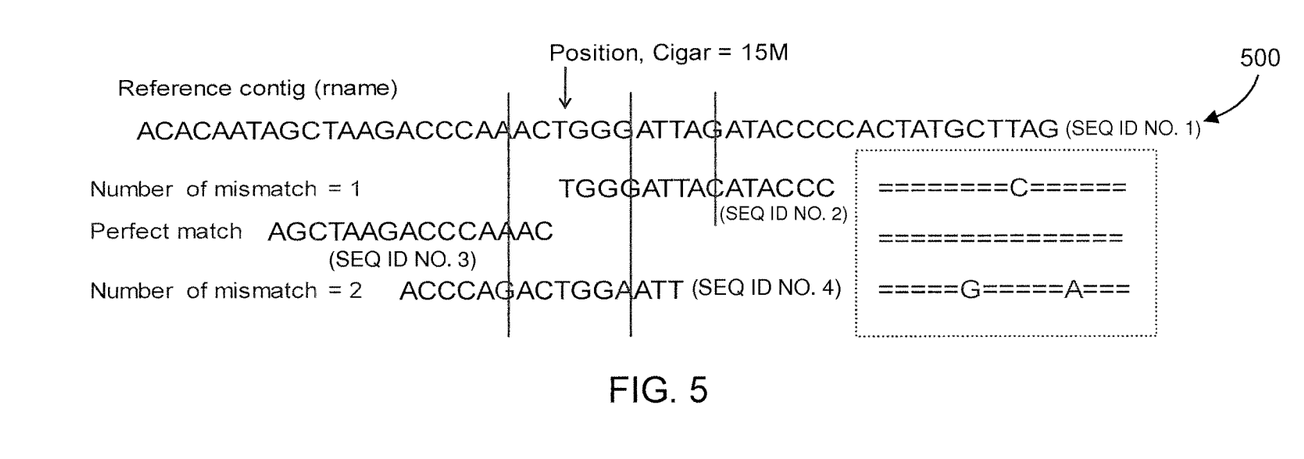
FIG. 5 shows an exemplary alignment 500 of a read sequence to a reference genome using cigar and rname fields in the header, in accordance with an embodiment of the present principles.
Figure 6:
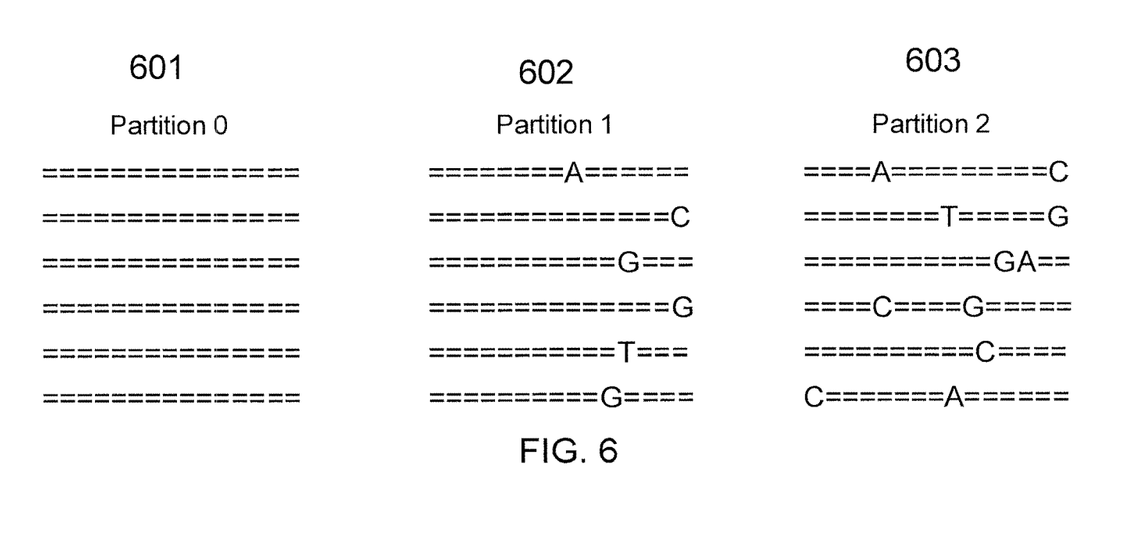
FIG. 6 shows exemplary read sequences 601, 602, and 603 for partition 0, partition 1, and partition 2, respectively, in accordance with an embodiment of the present principles.
Figure 7:
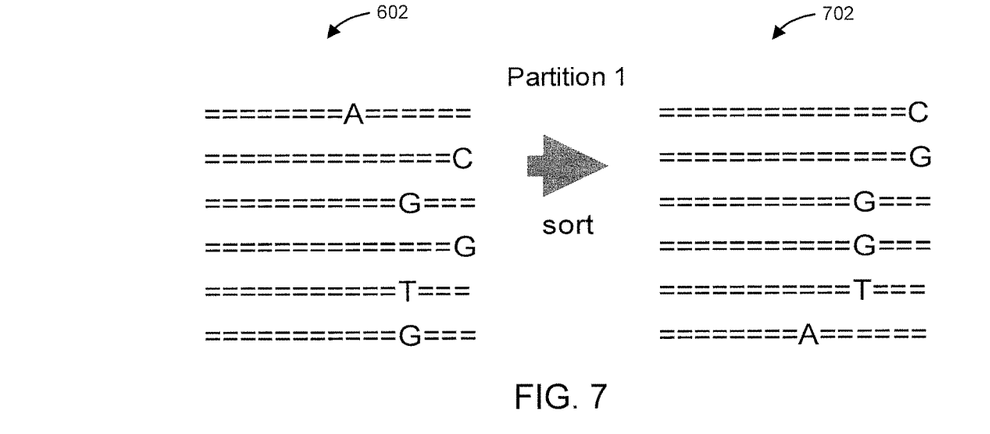
FIG. 7 show an exemplary classification and sorting 702 of read sequences 602 for partition 1 based on the positions (indexes) of mismatched bases within the sequence 602, in accordance with an embodiment of the present principles.
Figure 8:
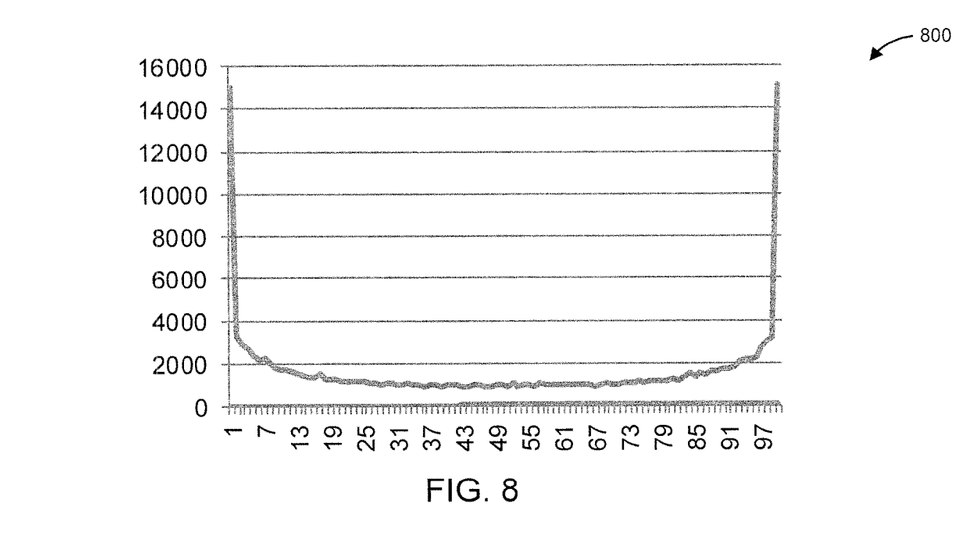
FIG. 8 shows an exemplary histogram 800 built based on index of a mismatched base for the group with a single mismatched base, in accordance with an embodiment of the present principles.
Figure 9:
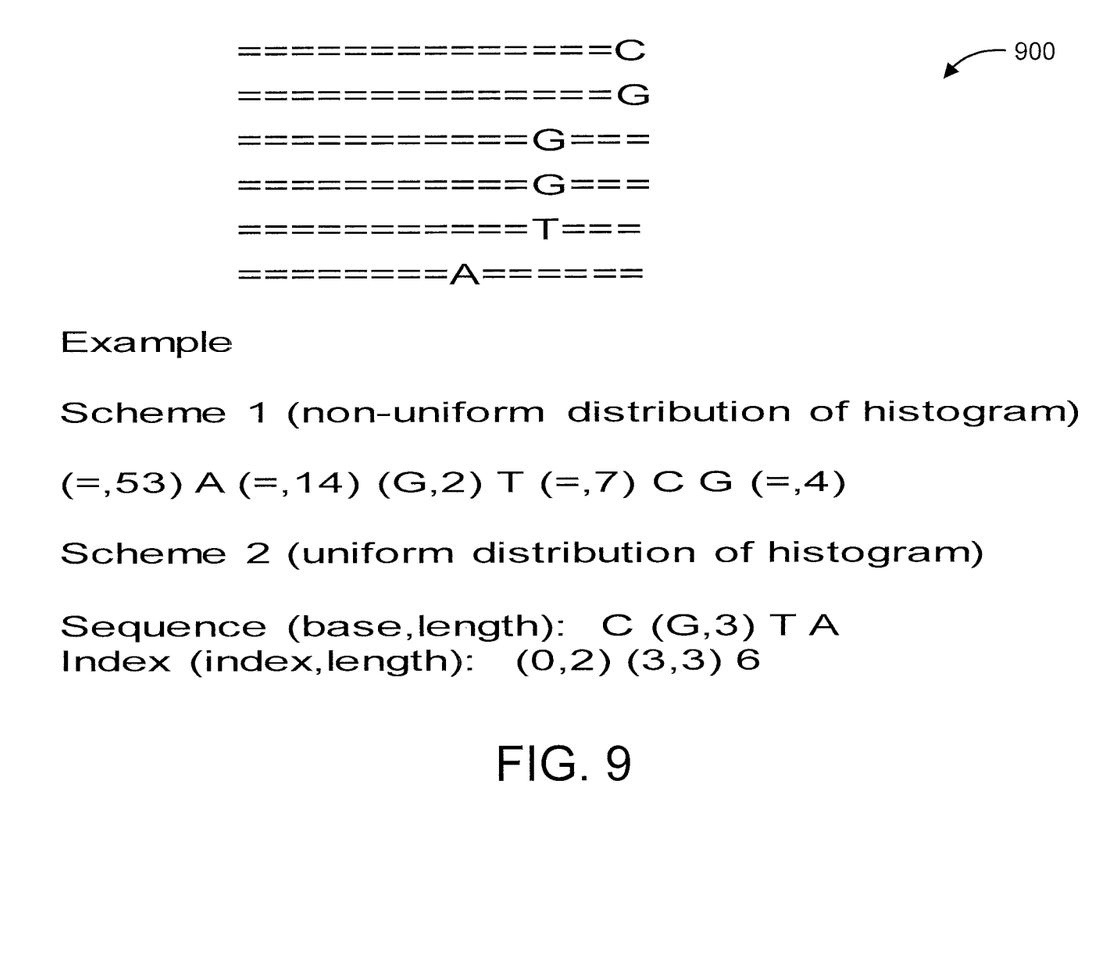
FIG. 9 shows an exemplary result of run-length coding for coding scheme 1 and coding scheme 2.

The preceding steps 410, 420, 440, and 460 of method 400 are also shown with respect to FIGS. 4 through 9, respectively. Step 410 corresponds to FIG. 5. Step 420 corresponds to FIGS. 6 and 7. Blocks 431, 432, and 433 correspond to FIGS. 6 and 7. Step 440 corresponds to FIG. 8. Steps 452 and 453 correspond to FIG. 9. In particular, FIG. 5 shows an exemplary alignment 500 of a read sequence to a reference genome using cigar and rname fields in the header, in accordance with an embodiment of the present principles. FIG. 6 shows exemplary read sequences 601, 602, and 603 for partition 0, partition 1, and partition 2, respectively, in accordance with an embodiment of the present principles. FIG. 7 show an exemplary classification and sorting 702 of read sequences 602 for partition 1 based on the positions (indexes) of mismatched bases within the sequence 602, in accordance with an embodiment of the present principles. The sequences with mismatched indexes at the same positions are lexicographically sorted. FIG. 8 shows an exemplary histogram 800 built based on the position of mismatches within a read sequence when number of mismatched base is one, in accordance with an embodiment of the present principles. Referring to FIGS. 3 through 9, after the read sequences are parsed from the SAM file 310, each read sequence is mapped to the reference genome 320 (FIG. 5). Based on the mapping results, the read sequences are classified into a number of groups of read sequences depending on the number of mismatched bases within the sequence (FIG. 6). Since most of the read sequences are perfectly or near-perfectly matched with the reference genome using the mapping position and pattern information, most of the read sequences belong to only several groups. For example, about 70% of read sequences belong to a perfectly matched group with the number of mismatched bases equal to zero. As noted above, FIG. 6 depicts exemplary groups of read sequences. The read sequences include read sequences 601, 602 and 603, where read sequences 601 have the number of mismatched bases equal to zero (perfectly matched), read sequences 602 one mismatched base (every read base is matched except one read base), and read sequences 603 have two mismatched bases. The matched bases are replaced with a character "=". Furthermore, to maximize the length of stretches of "=" characters, the classified read sequences are sorted within each group based on the position of mismatched base as depicted in FIG. 7. If there are multiple sequences with same mismatched base index, the sequences are lexicographically sorted. Since a run-length is basically a pair consisting of a single character and a positive integer number that indicates the run length of the character, the entireties of the sequences within the perfectly matched group (70% of total read sequences) can be encoded with zero bit spending. The efficiency of run-length coding is improved when number of mismatched base is more than one by sorting the sequences in the group to have the length of column-wise stretch of '=' longer. As depicted in FIG. 8, a histogram is built based on mismatched base indexes. The distribution of indexes decides how the read sequences will be encoded. If the indexes are uniformly distributed along one hundred possible positions, the read sequences are encoded in two strings of symbols based on run-length coding. The values of mismatched bases and positions of the mismatched bases are encoded using run-length coding independently into two separate bit streams. If the distribution of indexes is not uniformly distributed with a couple of peaks as depicted in FIG. 8, it means that there are many sequences having same mismatched positions, and column-wise run-length coding works well. The two coding schemes are illustrated in FIG. 9.

The compression ratio of the proposed method is compared with a general compression algorithm (GZIP) and CRAM lossless compression mode in TABLE 1. The proposed method significantly outperforms CRAM in compressing header and read sequences, for example 26:1 (CRAM) versus 92:1 (proposed method) with SRR702072 as an input sequence.

TABLE 1

| Sequence | GZIP | CRAM | proposed |
|---|---|---|---|
| SRR062634 | 3.9 | 20 | 43 |
| SRR043384 | 4.0 | 16 | 34 |
| SRR081241 | 3.9 | 23 | 66 |
| SRR077487 | 3.9 | 23 | 65 |
| SRR037780 | 4.2 | 17 | 39 |
| SRR100335 | 3.7 | 18 | 37 |
| SRR702072 | 3.9 | 26 | 92 |
| ERR013151 | 3.7 | 19 | 41 |

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A processor-implemented method for lossless compression of DNA sequences, comprising:

executing efficient run-length coding and improving compression performance of the DNA sequences by preprocessing a plurality of read sequences and omitting storing of qname field information for compressing paired-end DNA reads, respectively, the preprocessing comprising:

aligning a reference genome with a plurality of DNA sequences, each of the plurality of DNA sequences having a respective plurality of bases;

classifying and sorting the plurality of read sequences into a plurality of partitions based on respective numbers of mismatched bases within the plurality of read sequences to obtain a plurality of re-arranged DNA sequences, with the read sequences including stretches of identical characters, the partitions including a first partition including only matched sequences, a second partition including only mismatched base sequences, and a third partition including more than one mismatched base sequence;

building a histogram based on respective positions of mismatched bases within the plurality of re-arranged DNA sequences; and run-length coding at least some of the plurality of re-arranged DNA sequences based on the histogram, wherein values and positions of the mismatched bases are independently encoded into separate bit streams using the run-length coding, and an analysis of a distribution of indexes in the histogram determines a type of run-length coding for run-length coding the sequences, the coding further comprising performing the lossless compression of DNA sequences stored in a reference based Sequence Alignment Map (SAM) file format based on the preprocessing, the preprocessing including the aligning, the classifying, and the building.

2. The method of claim 1, wherein said aligning step aligns the reference genome with the plurality of DNA sequences using header data from a Sequence Alignment Map file.

3. The method of claim 2, wherein the header data comprises cigar and rname fields from the Sequence Alignment Map file.

4. The method of claim 1, wherein each of the plurality of DNA sequences is classified and sorted based on the respective index corresponding thereto.

5. The method of claim 4, wherein particular ones of the plurality of DNA sequences having a same index are sorted lexicographically.

6. The method of claim 1, wherein the histogram comprises a plurality of bins, each of the plurality of bins representing a respective index of mismatched base positions within respective ones of at least some of the plurality of re-arranged DNA sequences.

7. The method of claim 1, wherein the histogram includes mismatched base data only for corresponding ones of the plurality of re-arranged DNA sequences with a single mismatched base, and a particular coding scheme used to code the corresponding ones of the plurality of re-arranged DNA sequences is selected from among a plurality of available coding schemes responsive to an overall distribution of the histogram for the corresponding ones of the plurality of re-arranged DNA sequences.

8. The method of claim 1, wherein said coding step codes the plurality of re-arranged DNA sequences column-wise using run-length coding.

9. The method of claim 1, wherein only metadata is coded for any of the plurality of re-arranged data sequences without mismatched bases.

10. The method of claim 1, wherein at least some of the plurality of re-arranged DNA sequences are coded using different encoding techniques with respect to each other depending upon a distribution of the histogram.

11. A non-transitory article of manufacture tangibly embodying a computer readable program which when executed causes a computer to perform the steps of claim 1.

12. An apparatus for lossless compression of DNA sequences, comprising:
one or more processor devices configured to execute efficient run-length coding and improve compression performance of the DNA sequences by preprocessing a plurality of read sequences and omitting storing of qname field information for compressing paired-end DNA reads, respectively, the preprocessing comprising:
aligning, using a sequence aligner, a reference genome with a plurality of DNA read sequences, each of the plurality of DNA read sequences having a respective plurality of bases;
classifying and sorting, using a sequence classifier and sorter, the plurality of read sequences into a plurality of partitions based on respective numbers of mismatched bases within the plurality of read sequences to obtain a plurality of re-arranged DNA read sequences, with the read sequences including comparatively long stretches of identical characters, the partitions including a first partition including only matched sequences, a second partition including only mismatched base sequences, and a third partition including more than one mismatched base sequence;
building a histogram, using a histogram builder, based on indexes of mismatched bases within the plurality of re-arranged DNA read sequences; and
a processor-based coder for run-length coding at least some of the plurality of re-arranged DNA read sequences based on the histogram, wherein values and positions of the mismatched bases are independently encoded into separate bit streams using run-length coding, and an analysis of a distribution of indexes in the histogram determines a type of run-length coding for run-length coding the sequences, the coder being further configured to perform lossless compression of the DNA sequences stored in a reference based Sequence Alignment Map (SAM) file format based on the preprocessing, the preprocessing including the aligning, the classifying, and the building.

13. The apparatus of claim 12, wherein said sequence aligner aligns the reference genome with the plurality of DNA sequences using header data from a Sequence Alignment Map file.

14. The apparatus of claim 13, wherein the header data comprises cigar and rname fields from the Sequence Alignment Map file.

15. The apparatus of claim 12, wherein the sequence classifier and sorter classifies and sorts each of the plurality of DNA sequences based on the respective index corresponding thereto.

16. The apparatus of claim 15, wherein particular ones of the plurality of DNA sequences having a same index are sorted lexicographically.

17. The apparatus of claim 12, wherein the histogram comprises a plurality of bins, each of the plurality of bins representing a respective index of mismatched base positions within respective ones of at least some of the plurality of re-arranged DNA sequences.

18. The apparatus of claim 12, wherein the histogram includes mismatched base data only for corresponding ones of the plurality of re-arranged DNA sequences with a single mismatched base, and a particular coding scheme used to code the corresponding ones of the plurality of re-arranged DNA sequences is selected from among a plurality of available coding schemes responsive to an overall distribution of the histogram for the corresponding ones of the plurality of re-arranged DNA sequences.

19. The apparatus of claim 12, wherein said processor-based coder codes the plurality of re-arranged DNA sequences column-wise using run-length coding.

20. The apparatus of claim 12, wherein said processor-based coder only codes metadata for any of the plurality of re-arranged data sequences without mismatched bases.

* * * * *